United States Patent
Lösel et al.

[11] 3,981,992
[45] Sept. 21, 1976

[54] DERIVATIVES OF 3β-(4'-OXO-α-L-RHAMNOSYL)-14β-HYDROXY-BUFA-4,20,22-TRIENOLIDE

[75] Inventors: Walter Lösel, Ingelheim am Rhein; Werner Traunecker, Munster-Sarmsheim; Wolfgang Hoefke, Budenheim, all of Germany

[73] Assignee: Boehringer Ingelheim GmbH, Ingelheim am Rhein, Germany

[22] Filed: July 30, 1975

[21] Appl. No.: 600,433

[30] Foreign Application Priority Data
Aug. 5, 1974  Germany............................ 2437693

[52] U.S. Cl..................................... 424/182; 536/6
[51] Int. Cl.²..................................... A61K 31/705
[58] Field of Search.................. 260/210.5; 424/182

[56] References Cited
UNITED STATES PATENTS
3,743,633   7/1973   Goerlich et al.................... 260/210.5

Primary Examiner—Johnnie R. Brown
Assistant Examiner—Cary Owens
Attorney, Agent, or Firm—Hammond & Littell

[57] ABSTRACT
Compounds of the formula

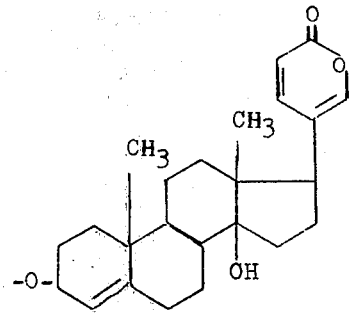

wherein
R is

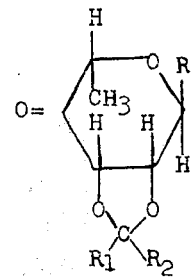

$R_1$ is hydrogen or alkoxy of 1 to 4 carbon atoms, and
$R_2$ is alkoxy of 1 to 4 carbon atoms, or
$R_1$ and $R_2$ together are oxygen;
the compounds are useful as cardiotonics.

9 Claims, No Drawings

DERIVATIVES OF 3β-(4'-OXO-α-L-RHAMNOSYL)-14β-HYDROXY-BUFA-4,20,22-TRIENOLIDE

This invention relates to novel 2',3'-substituted derivatives of 3β-(4'-oxo-α-L-rhamnosyl)-14β-hydroxy-bufa-4,20,22-trienolide, as well as to methods of preparing those compounds.

More particularly, the present invention relates to a novel class of 2',3'-substituted derivatives of 3β (4'-oxo-α-L-rhamnosyl)-14β-hydroxy-bufa-4,20,22-trienolide represented by the formula

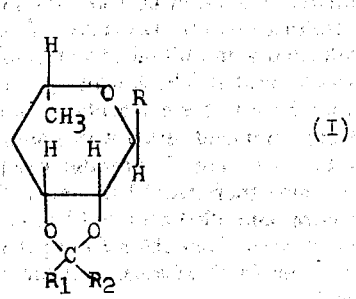
(I)

wherein
R is

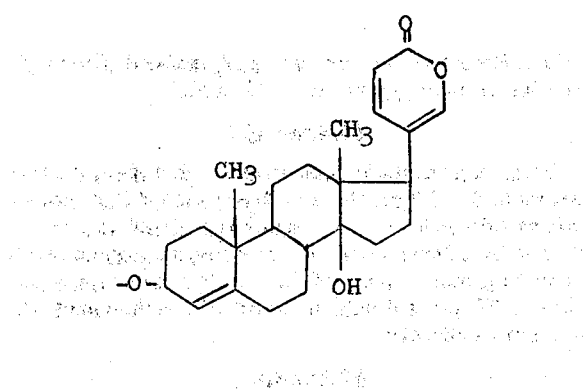

$R_1$ is hydrogen or alkoxy of 1 to 4 carbon atoms, and
$R_2$ is alkoxy of 1 to 4 carbon atoms, or
$R_1$ and $R_2$ together are oxygen.

The compounds embraced by formula I may be prepared by the following methods:

Method A

By oxidizing a compound of the formula

(II)

wherein R, $R_1$ and $R_2$ have the same meanings as in formula I.

The oxidation may be effected with dimethylsulfoxide in the presence of dicyclohexyl-carbodiimide and pyridinium chloride. This oxidation reaction is advantageously carried out at room temperature and optionally in the presence of an anhydrous, inert organic solvent. Examples of particularly suitable such solvents are aromatic hydrocarbons, such as benzene, or also ethyl acetate, because the dicyclohexylurea release by the reaction is insoluble in these solvent media and precipitates out. However, the oxidation with dimethylsulfoxide may also be performed in the presence of the pyridine-sulfur trioxide-complex and triethylamine.

Method B

By reacting 3β-(4'-oxo-α-L-rhamnosyl)-14-hydroxy-bufa-4,20,22-trienolide of the formula (III)

wherein R has the same meaning as is formula I, with an orthoester of the formula $$R_3C(OR_4)_3 \qquad (IV)$$

wherein
$R_3$ is hydrogen or alkoxy of 1 to 4 carbon atoms, and
$R_4$ is alkyl of 1 to 4 carbon atoms,
or with an active carbonic acid derivative, such as 1,1'-carbonyldiimidazole, benzyl imidazole-N-carboxylate, chlorocarbonic acid esters, phosgene or pyrocarbonic acid esters.

The transesterification of the compound of the formula III with a trialkyl orthocarboxylate or tetraalkyl orthocarbonate is carried out in the presence of an acid catalyst, such as p-toluenesulfonic acid.

The esterification of compound II with an active carbonic acid derivative is carried out in an inert anhydrous organic solvent at room temperature or moderately elevated temperatures, and in the presence of an acid-binding agent, if necessary.

Method C

For the preparation of a compound of the formula I wherein $R_1$ and $R_2$ together are oxygen, by hydrolysis of a corresponding compound of the formula I, wherein $R_1$ and $R_2$ are other than together oxygen, in the presence of an acid catalyst and in accordance with known procedures.

A starting compound of the formula II may be prepared by reacting proscillaridin A with a tetraalkyl orthocarbonate or a trialkyl orthoformate in the presence of an acid catalyst; or by reacting proscillaridin A with an active carbonic acid derivative, such as 1,1'-carbonyldiimidazole, benzyl imidazole-N-carboxylate, a chlorocarbonate, phosgene or a pyrocarbonate, in the presence of an acid-binding agent, if necessary.

A starting compound of the formula III may be obtained from a compound of the formula I by hydrolysis, preferably with a dilute acid or base, at room temperature or moderately elevated temperatures, and in an inert organic solvent.

The following examples illustrate the present invention and will enable others skilled in the art to understand it more completely. It should be understood, however, that the invention is not limited solely to the particular examples given below.

Preparation of starting compounds of the formula II

EXAMPLE A

2',3'-Methoxymethylidene-proscillaridin 5.31 gm (10 millinols) of proscillaridin were added to a solution consisting of 100 ml of absolute tetrahydrofuran, 3 ml of trimethyl orthoformate and 50 mgm of anhydrous p-toluenesulfonic acid, and the mixture was stirred at room temperature. The reaction went to completion after about 10 minutes, whereupon the reaction mixture was neutralized with triethylamine and evaporated to dryness in vacuo. The residue was crystallized from a mixture of ethyl acetate and petroleum ether (boiling point range to 40°–80°C), yielding 5.3 gm (93% of theory) of the compound of the formula

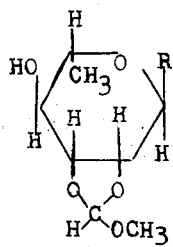

where R has the meaning previously defined. The product had a melting point of 135°–138°C.

EXAMPLE B

Using a procedure analogous to that described in Example A, 2.61 gm (89% of theory) of 2',3'-ethoxymethylidene-proscillaridin, m.p. 139°–141°C, were obtained by reacting 2.66 gm (5 millimols of proscillaridin with 2 ml of triethyl orthoformate and 20 mgm of anhydrous p-toluenesulfonic acid in 50 ml of absolute tetrahydrofuran, and crystallizing the raw reaction product from ethyl acetate/petroleum ether.

Preparation of end products of the formula I

EXAMPLE 1

3β-(2',3'-Methoxymethylidene-4'-oxo-α-L-rhamnosyl)-14β-hydroxy-bufa-4,20,22-trienolide by method A 650 mgm (6 millimols) of pyridene hydrochloride and 3.7 gm (18 millimols) of dicyclohexyl-carbodiimide were added to a solution of 1.720 gm (3 millimols) of 2',3'-methoxymethylidene-proscillaridin in 30 ml of absolute dimethylsulfoxide, and the resulting mixture was stirred for 1 to 2 hours at room temperature: the completion of the reaction was ascertained by thin-layer chromatography. Thereafter, the reaction mixture was admixed with 100 ml of ethyl acetate, the resulting mixture was suction-filtered, the filtrate was admixed with 500 ml of water, and the organic phase was separated. The aqueous phase was again extracted with 50 ml of ethyl acetate, and the organic phases were combined, dried with sodium sulfate and evaporated to dryness. The residue was purified on a silicagel column (grain size 0.2–0.5 mm) with a mixture of chloroform and ethyl acetate (2:1) as the eluant, and then crystallized from chloroform/petroleum ether, yielding 1.47 gm (86% of theory) of the compound of the formula

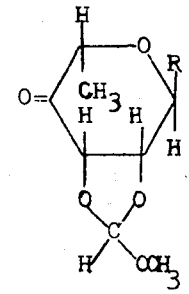

where R has the meaning previously defined. The product had a melting point of 213°–215°C.

EXAMPLE 2

Using a procedure analogous to that described in Example 1, 2.12 gm (87% of theory) of 3β-2',3'-ethoxymethylidene-4'-oxo-α-L-rhamnosyl)-14β-hydroxy-bufa-4,20,22-trienolide, an amorphous substance with a melting point range of 113°–115°C, were obtained from 2.35 gm (4 millimols) of 2',3'-ethoxymethylidene-proscillaridin.

EXAMPLE 3

3β-(2',3'-Dimethoxymethylidene-4'-oxo-α-L-rhamnosyl)-14β-hydroxy-bufa-4,20,22-trienolide by method A.

1.81 gm (3 millimols) of 2',3'-dimethoxymethylidene-proscillaridin were dissolved in a mixture consisting of 10 ml of dimethylsulfoxide and 5 ml of triethylamine, and the resulting solution was admixed with 1.75 gm (11 millimols) of pyridine-sulfur trioxide-complex in 10 ml of dimethylsulfoxide. The reaction mixture was stirred for about 30–50 minutes at room temperature, then diluted with ethyl acetate, admixed with about 10 times its volume of water, and finally washed successively with 2N hydrochloric acid, aqueous 5% sodium carbonate and water. The organic phase was subsequently dried with sodium sulfate and evaporated to dryness, and the residue was purified by chromatography on a silicagel column (grain size 0.2–0.5 mm) with a mixture of chloroform and ethyl acetate (3:1) as the eluant. The purified product was crystallized from ethyl acetate/petroleum ether, yielding 1.63 gm (68% of theory) of the compound of the formula

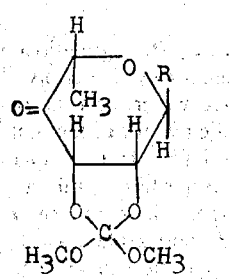

where R has the meaning previously defined. The product had a melting point of 190°–191°C.

EXAMPLE 4

Using a procedure analogous to that described in Example 1, 1.52 gm (81% of theory) of 3β-(2',3'-diethoxymethylidene-4'-oxo-α-L-rhamnosyl)-14β-hydroxy-bufa-4,20,22-trienolide, an amorphous substance with a melting point range of 106°–107°C, were obtained from 1.89 gm (3 millimols) of 2',3'-diethoxymethylidene-proscillaridin.

EXAMPLE 5

3β-(2',3'-Cyclocarbonyl-4'-oxo-α-L-rhamnosyl)-14β-hydroxy-bufa-4,20,22-trienolide by method C.

1.9 gm (3 millimols) of 3β-(2',3'diethoxymethylidene-4'-oxo-α-L-rhamnosyl)-14β-hydroxy-bufa-4,20,22-trienolide were dissolved in 50 ml of tetrahydrofuran, 1 ml of 2N hydrochloric acid was added to the solution, and the resulting mixture was stirred for 30 to 60 minutes at room temperature. The completion of the reaction was determined by thin-layer chromatography. After the reaction had gone to completion the reaction solution was neutralized with triethylamine and concentrated to a small volume by evaporation in vacuo, and the residue was taken up in a mixture of water and ethyl acetate. The organic phase was separated, dried over sodium sulfate and evaporated, and the residue was purified by chromatography on a silicagel column (grain size 0.2–0.5 mm) with chloroform-/acetone/ethyl acetate (70:15:15) as the eluant. 379 mgm (23.5% of theory) of the compound of the formula

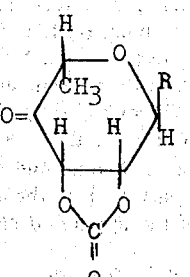

where R has the meaning previously defined, were obtained. $R_f$-value of product: 0.44 [Eluant: Chloroform/acetone (7:3); carrier: Silicagel plate].

$R_f$-value of starting material: 0.58 (eluant and carrier same as above).

The compounds of the present invention, that is, those embraced by formula I above, have useful pharmacodynamic properties. More particularly, the compounds of this invention exhibit cardiotonic, especially positive inotropic, activities in the isolated ventricle of the guinea pig heart and the heart-lung preparation, and are therefore useful for the treatment of cardiac insufficiencies in warm-blooded animals. The compounds are particularly superior over proscillaridin in that their absorption rate is significantly higher than that of the known cardiac glycoside.

Particularly preferred are those compounds of the formula I wherein $R_1$ is hydrogen and $R_2$ is methoxy or ethoxy.

In addition, by virtue of the reactive oxo-group on the rhamnose moiety, the compounds of this invention are useful as intermediates for the preparation of other cardiac glycoside derivatives.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective cardiotonic dosage unit of the compounds according to the present invention is from 0.00083 to 0.084 mgm/kg body weight, preferably from 0.002 to 0.034 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 6

Tablets

The tablet composition is compounded from the following ingredients:

| | | |
|---|---|---|
| 3β-(2-,3-Methoxymethylidene-4'-oxo-α-L-rhamnosyl)-14β-hydroxy-bufa-4,20,22-trienolide | 0.25 | parts |
| Lactose | 87.75 | " |
| Potato starch | 30.0 | " |
| Gelatin | 3.0 | " |
| Magnesium stearate | 1.0 | " |
| Total | 120.0 | parts |

Preparation

The glycoside is intensively milled with ten times its weight of lactose, the milled mixture is admixed with the remaining amount of the lactose and the potato starch, the resulting mixture is moistened with an aqueous 10% solution of the gelatin, the moist mass is forced through a 1.5 mm-mesh screen, and the resulting granulate is dried at 40°C. The dry granulate is again passed through a 1 mm-mesh screen, admixed with the magnesium stearate, and the composition is compressed into 120 mgm-tablets in a conventional tablet making machine. Each tablet contains 0.25 mgm of the glycoside and is an oral dosage unit composition with effective cardiotonic action.

EXAMPLE 7

Coated pills

The pill core composition is compounded from the following ingredients:

| | | |
|---|---:|---|
| 3β-(2',3'-Ethoxymethylidene-4'-oxo-α-L-rhamnosyl)-14β-hydroxy-bufa-4,20,22-trienolide | 0.25 | parts |
| Lactose | 32.25 | " |
| Corn starch | 15.00 | " |
| Polyvinylpyrrolidone | 2.00 | " |
| Magnesium stearate | 0.50 | " |
| Total | 50.0 | parts |

Preparation

The glycoside is intensively milled with ten times its weight of lactose, the milled mixture is admixed with the remainder of the lactose and the corn starch, the mixture is moistened with an aqueous 15% solution of the polyvinylpirrolidone, the moist mass is forced through a 1 mm-mesh screen, and the resulting granulate is dried at 40°C and again passed through the screen. The dry granulate is admixed with the magnesium stearate, and the resulting composition is compressed into 50 mgm-pill cores which are subsequently coated in conventional manner with a thin shell consisting essentially of a mixture of sugar and talcum and finally polished with beeswax. Each coated pill contains 0.25 mgm of the glycoside and is an oral dosage unit composition with effective cardiotonic action.

EXAMPLE 8

Drop Solution

The solution is compounded from the following ingredients:

| | | | |
|---|---|---:|---|
| 3β-(2',3'-Ethoxymethylidene-4'-oxo-α-L-rhamnosyl)-14β-hydroxy-bufa-4,20,22-trienolide | | 0.0125 | parts |
| Saccharin sodium | | 0.3 | parts |
| Sorbic acid | | 0.1 | " |
| Ethanol | | 30.0 | " |
| Flavoring | | 1.0 | " |
| Distilled water | q.s.ad | 100.0 | parts |

Preparation

The glycoside and the flavoring are dissolved in the ethanol, and the sorbic acid and the saccharin sodium are dissolved in the distilled water. The two solutions are uniformly admixed with each other, and the mixed solution is filtered until free from suspended matter. 1 ml of the filtrate contains 0.125 mgm of the glycoside and is an oral dosage unit composition with effective cardiotonic action.

EXAMPLE 9

Hypodermic solution

The solution is compounded from the following ingredients:

| | | | |
|---|---|---:|---|
| 3β-(2',3'-Cyclocarbonyl-4'-oxo-α-L-rhamnosyl)-14β-hydroxy-bufa-4,20,22-trienolide | | 0.25 | parts |
| Polyethyleneglycol 600 | | 700.0 | " |
| Tartaric acid | | 150.0 | " |
| Distilled water | q.s.ad | 3000.0 | " |
| | | | by vol. |

Preparation

The tartaric acid, the polyethyleneglycol and the glycoside are successively dissolved in a sufficient amount of distilled water, and the resulting solution is diluted with distilled water to the indicated volume and then filtered until free from suspended matter. The filtrate is filled into white 3 ml-ampules in an atmosphere of nitrogen, which are then sterilized for 20 minutes at 120°C and sealed. Each ampule contains 0.25 mgm of the glycoside, and the contents thereof are an injectable dosage unit composition with effective cardiotonic action.

EXAMPLE 10

Suppositories

The suppository composition is compounded from the following ingredients:

| | | |
|---|---:|---|
| 3β-(2',3'Methoxymethylidene-4'-oxo-α-L-rhamnosyl)-14β-hydroxy-bufa-4,20,22-trienolide | 0.25 | parts |
| Lactose | 4.75 | " |
| Suppository base (e.g. cocoa butter) | 1695.0 | " |
| Total | 1700.0 | parts |

Preparation

The glycoside and the lactose are admixed, and the mixture is milled. The milled mixture is uniformly stirred with the aid of an immersion homogenizer into the suppository base, which had previously been melted and cooled to 40°C. The resulting composition is cooled to 37°C, and 1700 mgm-portions thereof are poured into cooled suppository molds and allowed to harden therein. Each suppository contains 0.25 mgm of the glycoside and is a rectal dosage unit composition with effective cardiotonic action.

Analogous results are obtained when any one of the other compounds embraced by formula I was substituted for the particular glycoside in Examples 6 through 10. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula wherein R is

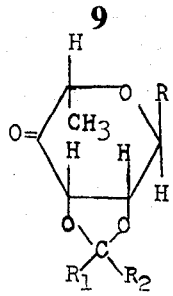

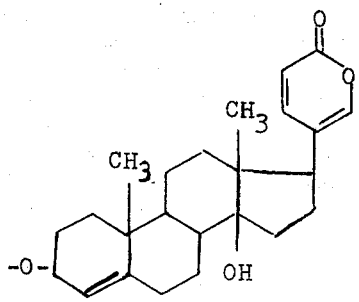

$R_1$ is hydrogen or alkoxy of 1 to 4 carbon atoms, and
$R_2$ is alkoxy of 1 to 4 carbon atoms, or
$R_1$ and $R_2$ together are oxygen.

2. A compound of claim 1, wherein $R_1$ is hydrogen, $R_2$ is methoxy or ethoxy, and R has the meaning defined in claim 1.

3. The compound of claim 1 which is 3β-(2',3'-methoxymethylidene-4'-oxo-α-L-rhamnosyl)-14β-hydroxy-bufa-4,20,22-trienolide.

4. The compound of claim 1 which is 3β-(2',3'-ethoxymethylidene-4'-oxo-α-L-rhamnosyl)-14β-hydroxy-bufa-4,20,22-trienolide.

5. The compound of claim 1 which is 3β-(2',3'-dimethoxymethylidene-4'-oxo-α-L-rhamnosyl)-14β-hydroxy-bufa-4,20,22-trienolide.

6. The compound of claim 1, which is 3β-(2',3'-diethoxymethylidene-4'-oxo-α-L-rhamnosyl)-14β-hydroxy-bufa-4,20,22-trienolide.

7. The compound of claim 1, which is 3β-(2',3'-cyclocarbonyl-4'-oxo-α-L-rhamnosyl)-14β-hydroxy-bufa-4,20,22-trienolide.

8. A cardiotonic pharmaceutical dosage unit composition consisting essentially of an inert pharmaceutical carrier and an effective cardiotonic amount of a compound according to claim 1.

9. The method of increasing the strength of the heart muscle contraction in a warm-blooded animal in need of such treatment, which comprises perorally, parenterally or rectally administering to said animal an effective cardiotonic amount of a compound according to claim 1.

* * * * *